(12) United States Patent
Forgez et al.

(10) Patent No.: US 8,771,691 B2
(45) Date of Patent: Jul. 8, 2014

(54) METHODS FOR THE TREATMENT AND THE PROGNOSTIC ASSESSMENT OF MALIGNANT PLEURAL MESOTHELIOMA

(75) Inventors: Patricia Forgez, Paris (FR); Marco Alifano, Paris (FR)

(73) Assignee: Inserm (Institut National de la Sante et de la Recherche Medicale), Paris (FR)

( * ) Notice: Subject to any disclaimer, the term of this patent is extended or adjusted under 35 U.S.C. 154(b) by 435 days.

(21) Appl. No.: 13/139,907

(22) PCT Filed: Dec. 14, 2009

(86) PCT No.: PCT/EP2009/067094
§ 371 (c)(1),
(2), (4) Date: Aug. 26, 2011

(87) PCT Pub. No.: WO2010/069929
PCT Pub. Date: Jun. 24, 2010

(65) Prior Publication Data
US 2011/0300161 A1    Dec. 8, 2011

(30) Foreign Application Priority Data

Dec. 18, 2008  (EP) .................................... 08305971

(51) Int. Cl.
*A61K 31/00* (2006.01)
*A61K 38/00* (2006.01)
*A61K 39/395* (2006.01)
*A61K 49/00* (2006.01)
*A01N 61/00* (2006.01)
*A61B 5/055* (2006.01)

(52) U.S. Cl.
USPC ......... 424/138.1; 424/9.1; 424/9.2; 424/9.34; 424/130.1; 514/1; 514/1.1; 514/19.2; 514/19.3

(58) Field of Classification Search
None
See application file for complete search history.

(56) References Cited

PUBLICATIONS

Rihn, B.H. et al. Differential gene expression in mesothelioma. FEBS Letters 480: 95-100, 2000.*
Alifano, Marco et al. Neurotensin expression and outcome of malignant pleural mesothelioma. Biochimie 92: 164-170, 2010.*
"MSTO-211H", Peptides Oct. 2006, [Online] XP002513646.
Evers, Peptides, 27(10):2424-2433 (2006) XP005661211.
Gully et al., Proc. Nat. Acad. Sci. USA, 90:65-69 (1993) XP002570667.
International Search Report and Written Opinion in PCT/EP2009/067094, dated Mar. 8, 2010.

* cited by examiner

*Primary Examiner* — Alana Harris Dent
(74) *Attorney, Agent, or Firm* — McAndrews, Held & Malloy Ltd.

(57) ABSTRACT

The present invention relates to methods for the treatment and the prognostic assessment of malignant pleural mesothelioma.

5 Claims, 4 Drawing Sheets

Figure 4

METHODS FOR THE TREATMENT AND THE PROGNOSTIC ASSESSMENT OF MALIGNANT PLEURAL MESOTHELIOMA The present application is filed pursuant to 35 U.S.C. 371 as a U.S. National Phase application of International Patent Application No. PCT/EP2009/067094, which was filed Dec. 14, 2009, claiming the benefit of priority to European Patent Application No. 08305971.7, which was filed on Dec. 18, 2008. The entire text of the aforementioned applications is incorporated herein by reference in its entirety.

FIELD OF THE INVENTION

The present invention relates to methods for the treatment and the prognostic assessment of malignant pleural mesothelioma.

BACKGROUND OF THE INVENTION

Malignant pleural mesothelioma (MPM) is a relatively infrequent disease, whose incidence is estimated in western countries between less than 1 case/million/year among persons non exposed to asbestos and 100 cases/million/year among individuals professionally exposed to asbestos. The incidence of disease is expected to continue to increase in the next years, with a peak between 2015 and 2020.

Prognosis of MPM is generally poor: a recent study showed that in a comprehensive unselected population, median survival was 8.9 months. Reports from referral institutions concerning patients participating to clinical trials showed a slightly better outcome. A randomized study comparing mono-chemotherapy with cisplatin to the association cisplatin-pemetrexed (an antifolate drug) showed a median survival of 9.3 months and 12.1 months in the two arms, respectively, this later drug association is now considered the standard of care. Nevertheless, these results are globally discouraging because of the very low rate of long term survival. More recently, a treatment strategy based on the association of induction chemotherapy and radical surgery by extrapleural pneumonectomy resulted in 5-year survival rate of approximately 40% in patients with epithelioid mesothelioma, complete (R0) resection, and no mediastinal nodes involvement. However, only a minority of patients with MPM can benefit from this aggressive therapeutic strategy, because of advanced disease, histological type, advanced age or co-morbidities. In current practice less than 40% of patients with MPM receive chemotherapy and the remaining ones are offered only supportive cares. Identification of new prognostic factors would help in the understanding of disease progression and thereby patient management.

SUMMARY OF THE INVENTION

There is provided a method for treating malignant pleural mesothelioma, comprising the step of administering an effective amount of an inhibitor of the neurotensin activation of the neurotensin receptor 1 (NTSR1) to a subject in need thereof.

The present invention also provides a method for treating malignant pleural mesothelioma, comprising the step of administering an effective amount of a cytotoxic agent which binds to the neurotensin receptor 1 to a subject in need thereof.

The present invention also relates to a method of determining the prognosis of a subject suffering from malignant pleural mesothelioma, comprising the step of detecting the expression of neurotensin (NTS) in a mesothelioma sample obtained from said subject. The expression of NTS is associated with a worse prognostic, i.e. a lowest survival rate.

DETAILED DESCRIPTION OF THE INVENTION

The present invention provides a method for treating malignant pleural mesothelioma, comprising the step of administering an effective amount of an inhibitor of the neurotensin activation of the neurotensin receptor 1 (NTSR1) to a subject in need thereof.

Also provided is an inhibitor of the neurotensin activation of the neurotensin receptor 1 (NTSR1) for the treatment of malignant pleural mesothelioma.

The expression "inhibitors of the neurotensin activation of NTSR1" should be understood broadly, this expression refers to agents down-regulating the expression of neurotensin or of neurotensin receptor 1, compounds that bind to neurotensin (NTS) or NTSR1 and inhibit the neurotensin activation of NTSR1, or a protease that can degrade NTS.

Examples of inhibitors of the neurotensin activation of NTSR1 may be selected from the group consisting of an agent down-regulating the expression of neurotensin or of neurotensin receptor 1, an antibody against neurotensin or a fragment thereof which binds to neurotensin, an antibody against the neurotensin receptor 1 or a fragment thereof which binds to the neurotensin receptor 1, an antagonist of the neurotensin receptor 1, and a protease that can degrade NTS.

In an embodiment of the present invention, the inhibitor of the neurotensin activation of the neurotensin receptor 1 is an agent down-regulating the expression of neurotensin or of neurotensin receptor 1 in mesothelioma cells. Typically, agent down-regulating the expression of neurotensin or of neurotensin receptor 1 comprises a nucleic acid which interferes with the expression of neurotensin or of neurotensin receptor 1.

Typically, the down-regulation of the NTS or NTRS1 expression may be measured by immunohistochemistry, binding assay, mRNA level for NTSR1 and radio-immunoassay or Enzyme link immunosorbent assay for NTS (Holtom P E, et al J Neurosci Methods. 100(1-2):151-6, 2000; Davis L G et al, J Neurosci Methods 15-23, 1985; Vincent J P Ann N Y Acad. Sci., 668:90-100, 1992; Souazé F et al., J Biol Chem, 272(15):10087-94, 1997).

Examples of such agents are antisense molecules or vectors comprising said antisense molecules. Antisense molecules are complementary strands of small segments of mRNA. Methods for designing effective antisense molecules being well known (see for example U.S. Pat. No. 6,165,990), it falls within the ability of the skilled artisan to design antisense molecules able to downregulate the expression of neurotensin or of neurotensin receptor 1 in mesothelioma cells. Further examples are RNA interference (RNAi) molecules such as, for example, short interfering RNAs (siRNAs) and short hairpin RNAs (shRNAs). RNAi refers to the introduction of homologous double stranded RNA to specifically target a gene's product, in the present case neurotensin or of neurotensin receptor, resulting in a null or hypomorphic phenotype. Methods for designing effective RNAi molecules being well known (see for review Hannon and Rossi Nature. 2004 Sep. 16; 431(7006):371-8), it falls within the ability of the skilled artisan to design RNAi molecules able to downregulate the expression of neurotensin or of neurotensin receptor in mesothelioma cells.

Examples of siRNAs able to downregulate the expression of neurotensin or of neurotensin receptor in mesothelioma cells are nucleic acid molecules which comprise one of the following sequences:

```
siRNA NTSR1:
5'-AAGAAGTTCATCAGCGCCATC-3'      (SEQ ID NO: 1)

siRNA NTS:
5'-GCAATGTTGACAATATACC-3'        (SEQ ID NO: 2)
```

In a further embodiment of the invention, the inhibitor of the neurotensin activation of the neurotensin receptor 1 is an antibody against neurotensin or a fragment thereof which binds to neurotensin, an antibody against the neurotensin receptor 1 or a fragment thereof which binds to the neurotensin receptor 1.

The person skilled in the art will be aware of standard methods for production of such specific antibody or fragment thereof. For example, specific antibodies or fragment thereof may be generated by immunizing an animal with neurotensin or with NTSR1 and by selecting the antibodies which inhibit the neurotensin activation of the neurotensin receptor 1.

Typically the inhibition of the neurotensin activation of the neurotensin receptor 1 may be measured with biological assays estimating the second messenger level, or the oncogenic cellular effect, or the morphological changes of the cells (Skrzydelski D et al Mol. Pharmacol. 64(2):421-9 2003; Xu-van Opstal W Y et al, Microsc Res Tech. 28(5):440-7 1994; Souaze F et al. Can Res 66(12):6243-9 2006).

The person skilled in the art will be aware of standard methods for production of both polyclonal and monoclonal antibodies and fragments thereof which binds to NTS or to NTSR1. Antibody fragments, particularly Fab fragments and other fragments which retain epitope-binding capacity and specificity are also well known, as are chimeric antibodies, and "humanized" antibodies, in which structural (not determining specificity for antigen) regions of the antibody are replaced with analogous or similar regions from another species. Thus antibodies generated in mice can be "humanized" to reduce negative effects which may occur upon administration to human subjects. Chimeric antibodies are now accepted therapeutic modalities with several now on the market. The present invention therefore comprehends use of antibody specific for neurotensin or NTSR1 which include F(ab')$_2$, F(ab)$_2$, Fab, Fv and Fd antibody fragments, chimeric antibodies in which one or more regions have been replaced by homologous human or non-human portions. The person skilled in the art will also be aware that fragments such as for example ScFv fragments and divalent ScFv-type molecules can be prepared using recombinant methods.

In a further embodiment of the present invention, the inhibitor of the neurotensin activation of the neurotensin receptor 1 is an antagonist of the neurotensin receptor 1. Antagonists of the neurotensin receptor 1 are well known. SR48692 SR14294A are commonly used inhibitors of NTSR1 (see for example Gully et al. 1993, Proc. Natl. Acad. Sci. 90, 65-69 and Gully et al. 1997, J. Pharmacol. Exp. Ther. 280, 802-812). WO96/32382, WO95/32218, U.S. Pat. No. 5,430,047, U.S. Pat. No. 5,668,279 and EP0699438, for example, disclose families of antagonists of the neurotensin receptor 1.

In a further embodiment of the invention, the inhibitor of the neurotensin activation of the neurotensin receptor 1 is a protease that can degrade NTS. Examples of proteases that can degrade NTS are mast Cell carboxypeptidase A, neurolysin or human skin chymase. The protease may be administered to the subject in need thereof in its proteineous form or by gene therapy, for example by using a vector which enables the expression of the protease in situ.

The expression of NTSR1 by mesothelioma cells enables the specific targeting of mesothelioma cells with a cytotoxic agent which binds to the neurotensin receptor 1.

The present invention provides a method for treating malignant pleural mesothelioma, comprising the step of administering an effective amount of a cytotoxic agent which binds to the neurotensin receptor 1 to a subject in need thereof.

Also provided is a cytotoxic agent which binds to the neurotensin receptor 1 for the treatment of malignant pleural mesothelioma.

Examples of cytotoxic agents which bind to the neurotensin receptor 1 may be selected from the group consisting of an antibody against the neurotensin receptor 1 or a fragment thereof which binds to the neurotensin receptor 1, neurotensin or a neurotensin analogue conjugated with a cytotoxic drug, and neurotensin or a neurotensin analogue labelled with a cytotoxic radioisotope. The cytotoxic agent which binds to the neurotensin receptor 1 may also be an antimetabolite.

Typically said antibody against the neurotensin receptor 1 or said fragment thereof which binds to the neurotensin receptor 1, may be conjugated with a cytotoxic drug or labelled with a cytotoxic radioisotope.

Alternatively, said antibody against the neurotensin receptor 1 or said fragment thereof which binds to the neurotensin receptor may trigger antigen-dependent cell-mediated cytotoxicity (ADCC) and/or complement dependent cytotoxicity (CDC). This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J. Immunol. 1992 May 1; 148(9):2918-22.).

Neurotensin analogues are well known, WO98/33531, WO00/78796, WO2007/093373, U.S. Pat. No. 6,312,661 and U.S. Pat. No. 5,760,188, for example, provide families of neurotensin analogues. The neurotensin analogue may be an antagonist or an agonist of NTSR1.

Examples of cytotoxic drugs are platinum salts, taxanes, vinca derivatives and analogues, gemcitabine, methotrexate, doxorubicin, cytotoxin such as Pseudomonas exotoxin, g protein, and g protein coupled receptor inhibitors.

Common cytotoxic radioisotopes are, for example, $^{131}$I, $^{90}$Y, $^{77}$Lu, $^{67}$Cu, $^{186}$Re, $^{188}$Re, $^{212}$Bi and $^{213}$Bi.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of malignant pleural mesothelioma.

By a "therapeutically effective amount" of an inhibitor of the neurotensin activation of the neurotensin receptor 1 or of a cytotoxic agent which binds to the neurotensin receptor 1 is meant a sufficient amount to treat malignant pleural mesothelioma, at a reasonable benefit/risk ratio applicable to any medical treatment. It will be understood, however, that the total daily usage of the inhibitor or of the cytotoxic agent will be decided by the attending physician within the scope of sound medical judgment. The specific therapeutically effective dose level for any particular subject in need thereof will depend upon a variety of factors including the stage of malignant pleural mesothelioma being treated and the activity of the specific inhibitor/cytotoxic agent employed, the age, body weight, general health, sex and diet of the subject, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved.

Typically medicaments according to the invention comprise an inhibitor of the neurotensin activation of the neurotensin receptor 1 or a cytotoxic agent which binds to the neurotensin receptor 1, together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

A method of treatment according to the invention may be used in combination with any other therapeutic strategy for treating malignant pleural mesothelioma, e.g. surgery, (pleurectomy, pleurectomy-decortication or pleuro-pneumonectomy), chemotherapy or or targeted therapies (inhibition of growth factors pathways).

Typically, before applying a method of treatment according to the present invention to a subject suffering from malignant pleural mesothelioma, a diagnostic test may be performed in order to determine whether the malignant pleural mesothelioma displays NTS-expressing cells. By performing such a pre-treatment diagnostic test, it is possible to determine whether a subject would be responsive to a method of treatment according to the invention.

It falls within the ability of the skilled artisan to carry out such a diagnostic test. Typically NTS expression may be measured for example by RT-PCR or immunohistochemistry performed on a pleural sample obtained by biopsy.

Alternatively, levels of neurotensin or a precursor thereof such as proneurotensin in a sample obtained from the subjects may be determined in order to treat only those subjects having an elevated level of neurotensin or a precursor thereof such as proneurotensin. Examples of samples obtained from the subjects are whole blood sample, plasma sample or serum sample, as well as whole blood, serum or plasma samples obtained from samples collected from peritumoral veins (e.g. intercostal or azygos veins). Neurotensin or proneurotensin survey may also be used to detect an eventual recurrence of the tumor and/or of metastases. Examples of method for measuring the levels of proneurotensin are given in WO2006/079528, in Ernst et al., Peptides 27 (2006) 1787-1793 and in Friry et al, Biochemical and Biophysical research Communication 290, 1161-1168 (2002).

The present invention also relates to a method of determining the prognosis of a subject suffering from malignant pleural mesothelioma, comprising the step of detecting the expression of NTS in a mesothelioma sample obtained from said subject.

The expression of NTS is associated with a worse prognostic, i.e. a lowest survival rate.

The present invention also enables the evaluation of the risk of recurrence of a subject which has been surgically treated.

The term "detecting" as used above includes qualitative and/or quantitative detection (measuring levels) with or without reference to a control. Typically NTS expression may be measured for example by RT-PCR or immunohistochemistry performed on a pleural sample obtained by biopsy. Alternatively, levels of neurotensin or a precursor thereof such as proneurotensin in whole blood sample, plasma sample or serum sample obtained from the subjects may be determined. Alternatively, levels of neurotensin or a precursor thereof such as proneurotensin in whole blood, serum or plasma samples obtained from samples collected from peritumoral veins (e.g. intercostal or azygos veins) may be determined.

A method of prognosis according to the invention may be used in combination with any other methods already used for the prognostic assessment of malignant pleural mesothelioma, including stage, demographic and antropometric parameters, results of routine clinical or laboratory examination, assessment of mesothelin and osteopontin.

In the following, the invention will be illustrated by means of the following examples as well as the figures.

FIGURE LEGENDS

Kaplan-Maier analysis and comparison made by the log-rank test was performed (A) on groups with positive (1) or negative (0) for NTSR1 expression; (B) on groups with t absence (1), moderate (2) or strong (3) expression for NTS (B).

A) NTS and NTSR1 transcript analysis. RNA from LNM35 (lane 1 and 3) and MSTO-211H (lane 2 and 4) were reverse-transcribed and PCR was performed as described in the experimental procedures. B) Effect of NTSR1 antagonist on MSTO-211H cellular growth. Cells were treated with $10^{-6}$ M SR 48692 or with $10^{-4}$ M DMSO, cells were counted after 24, 48, and 72 h of growth. Results represent the percentage of cells for each time point, compared to the number of cells initially seeded in the culture dishes. C) Effect of NTSR1 blockade on invasive activity of MSTO-21H cells. NTSR1 activity was blocked either with 5 $10^{-6}$ M SR 48692 or 1/50 dilution NTS antibody. Results represent the percentage of invasive cells compared to the number of cells seeded on the type I collagen coated inner membrane. Results represent the mean±SEM from three independent experiments for cellular growth and invasion assay.

A) Example of wound healing assay: initial gap (T0) and remaining gap (T30h) of cells treated or not with SR 48692 or in the presence of SR 48692 solvent is shown. The black marks allow relocating the wound after the first measure. B) Percentage of remaining gap was calculated for control cells, or DMSO or SR 48692 treated cells. Remaining gap is the distance of the open wound after 24 or 30 h compared to the initial wound. Results represent the mean±SEM from three independent experiments. ***, $P<0.001$

EXAMPLE

In the following description, all molecular biology experiments for which no detailed protocol is given are performed according to standard protocol.

SUMMARY

In this example, we studied the expression of both NTS and NTSR1 in a series of consecutive patients treated for malignant pleural mesothelioma in a curative intent, and evaluated the possible impact on prognosis of the expression of these molecules. Furthermore, using mesothelioma cell line, we demonstrated the effects of the inhibition of the neurotensinergic system on cellular migration and collagen invasion.

Methods: A series of 52 consecutive patients with malignant mesothelioma undergoing management with curative intent were studied by immunochemistry for the expression of NTS and NTSR1. In vitro cell migration and wound healing were performed on the mesothelioma cell line, MSTO-211H.

Results: Immunohistochemistry revealed that NTS and NTSR1 expression was found in 71.1% and 90.4% of malignant mesotheliomas, respectively. Expression of NTS was significantly ($p=0.015$) correlated with prognosis, with median survivals of 11.0 months, 18.4 months, and 29.8 months in patients showing expression scored as 2, 1, and 0, respectively. Multivariate analysis showed that expression of NTS ($p=0.007$) and non surgical therapy ($p=0.004$) were independent predictors of worse prognosis. In vitro studies showed that inhibition of the NTS system resulted in a significant reduction of both migration and collagen invasion of mesothelioma cells.

CONCLUSION

The expression of NTS is identified as a prognostic marker in patients with malignant pleural mesothelioma. Furthermore, using mesothelioma cell line, we demonstrated the effects of the inhibition of the neurotensinergic system on cellular migration and collagen invasion. Due to its contribution in mesothelioma progression, neurotensinergic system represents a target of choice for the treatment malignant pleural mesothelioma.

Methods

Patients

Clinical files of patients treated at the Thoracic Surgery Department of Hotel-Dieu Hospital, Paris, France, between 2002 and 2006 for malignant pleural mesothelioma were retrospectively reviewed. Among these patients, those responding to the following criteria were selected: 1) histological diagnosis on samples obtained at video-assisted thoracoscopy 2) subsequent treatment by either chemotherapy alone (associating Cisplatin and Pemetrexed) or by induction chemotherapy followed by extrapleural pneumonectomy 3) no death related to the treatment (chemotherapy or surgery). In almost all cases talc poudrage had been performed during the same operative time as video-assisted thoracoscopy. 26 patients with recurrent idiopathic spontaneous pneumothorax treated by video-assisted thoracoscopy were used as controls.

Tissue Specimens and Immunohistochemistry

For all cases new histologic slides of tumors were obtained by the paraffin wax embedded tissues stocked in the Pathology Department. Standard H&E staining was used to ensure the tumoral character of the specimen, and adjacent sections were obtained for immunohistochemistry. Immunostaining of NTS and NTSR1 was carried out on 4 μm thick deparaffinized sections, using the avidin biotin peroxidase complex method, as previously described (Souaze et al. Cancer Res 2006; 66:6243-6249). After inhibition of endogenous peroxidases with 3% hydrogen peroxide, slides were washed in TBS and incubated with 10% normal rabbit serum at room temperature (RT) for 30 min. NTS immunoreactivity was conducted using rabbit antibody directed against NTS (1/500) (NA1230 Biomol, USA) for 2 hours at RT in a humidified chamber for tumor. NTSR1 immunoreactivity was detected using a goat polyclonal antibody directed against the human carboxy terminus of the receptor (1:100) (C-20 Santa Cruz USA). All slides were rinsed three times with TBS; sections were incubated with biotinylated secondary antibody (1:200) (Vector, USA), for 30 min at RT. The antigen-antibody complex was revealed with avidin-biotin-peroxidase complex, for 30 min, according to the manufacturer's instructions for the Vectastain ABC Kit (Vector, USA). Staining was done for 5 min with diamino-benzidine tetrahydrochloride (DAB) (Sigma, USA). All slides were counterstained with hematoxylin. All specimens were scored by an anatomopathologist (unaware of treatment modalities and states at follow up) as follows: 0: positive staining <10% of tumor cells; 1: positive staining involving >10% and less than 50% of tumor cells; 2: strong positive staining involving more than 50% of tumor cells.

Culture Procedures

The human mesothelioma cell line, MSTO-211H, was selected because of its intense proliferative activity and its aggressive profile (ATCC CRL-2081, 211H). The MSTO-211H cells were grown in RPMI-1640 medium (Invitrogen, USA) supplemented with 10% fetal calf serum (PAATM) and 2 mM glutamine (Gibco®). Cells were stored at 37° in 5% $CO_2$ atmosphere.

RNA Extraction and RT-PCR

The protocols for total RNA extraction, reverse-transcription reaction (RT), and PCR are documented in Souazé et al; J Biol Chem 1997; 272:10087-10094. RT was performed on 1 μg of total RNA using a specific NTSR1 primer (5'-GCTGACGTAGAAGAG-3' SEQ ID NO:3) or 50 pmol of oligo dT and oligo dN. The PCR amplification was performed on a 1:5 v/v of the RT reaction using 25 pmol of each primer 5'-CGTGGAGCTGTACAACTTCA-3' SEQ ID NO:4 and 5'-CAGCCAGCAGACCACAAAGG-3' SEQ ID NO:5 for NTSR1, and 5'-AAGCACATGTTCCCTCTT-3' SEQ ID NO:6 and 5'-CATACAGCTGCCGTTTCAGA-3' SEQ ID NO:7 for NTS, and 1 unit of Taq polymerase (ABgene™, France). The amplification profile consisted of denaturation at 94° C. for 30 s, annealing at 57° C. for 45 s, and extension at 72° C. for 45 s. The PCR cycle were preceded by denaturation at 95° C. for 15 min and were followed by a final extension at 72° C. for 7 min Amplification was performed in a DNA thermal cycler 9700 (Perkin Elmer Applied Biosystems, Courtaboeuf, France).

Cellular Growth

Cellular growth was performed using 6 well-tissue-culture dishes. $15 \times 10^4$ MSTO-211H cells were seeded, after 24 h cells were washed twice with PBS, and complete media containing either $10^{-6}$M SR 48692, a NTSR1 antagonist, or $10^{-4}$M de DMSO was added to the cells. After 24, 48, and 72 h of growth, cells were trypsinized and counted with a cells coulter (Z1 Coulter® Particle Counter, Beckman Coulter™).

Wound Healing Assay

In order to evaluate the impact of the neurotensinergic system on cell migration, a wound healing assay was performed. $1.75 \times 10^6$ MSTO-211H cells were plated per well in 6 well dishes containing the medium in order to reach confluence. After 24 hours cells were serum-starved and scarification was performed in a Moscona buffer with a 20 μl pipette tip. Cells were maintained in culture with low serum medium (0.5% FCS) and treated with $10^{-6}$ M SR48692. Control cells were exposed or not to the SR48692 solvent, DMSO. Pictures were taken at the beginning and 24 and 30 hours later with a photonic microscope. The "remaining gap" was calculated as percentage between wound size at 30 hours and initial wound size.

Collagen Invasion Assay

Collagen invasion assay was performed by using tissue culture inserts composed of a 8 μm porous polycarbonate membrane, placed as inner chamber in 24 well-tissue-culture dishes. This membrane was coated with 404 of 2 mg/ml type I collagen diluted in RPMI-1640 medium (Collagen type I, rat tail, Upstate). The bottom chamber was filled with 500 μL RPMI-1640 medium supplemented with 10% fetal calf serum and 2 mM glutamine. $10^3$ MSTO-211H cells were seeded on the top of the inner chamber. Cells were treated with $5\times10^{-6}$ M of NTSR1 antagonist SR48692 or with 1:50 solution of anti-NTS rabbit antibody (NA1230, Tebu-Bio). Cells were placed for 48 hours at 37° C. in 5% $CO_2$ atmosphere. After incubation, non invasive cells on the upper surface of the collagen matrix were wiped off with cotton swabs. Filter membranes were fixed with 5% glutaraldehyde and remaining cells stained with 0.5% toluidine blue. Quantitation of invasive cells was carried out at the 400× magnification by using the software CELINA.

Statistical Analysis

Continuous variables were compared by the Wilcoxon or T test, as appropriate. Dicotomic variables were compared by the Chi-square or the Fisher exact test, as appropriate. Survival rates were calculated by the Kaplan-Meyer method and comparison of survival curves was performed with the log-rank test. All the available variables possibly influencing survival were used to carry out a multivariate analysis by using the Cox model. Statistical significance was accepted at p<0.05. The biochemical data were compared by Student's t test or of variances analysis followed by Neuman-Keuls test.

Results:

Fifty-two consecutive patients responding to the inclusion criteria were considered for the study. There were 34 men whose mean age was 66+10.5 years. Ten patients had a history of previously treated extrathoracic malignancy; 54% had a history of tobacco smoke and 45% of work exposition to asbestos. 44% of patients had unintentional loss of body weight >5% in the last three months; whereas 34% had a pre-operative CRP greater than 50 mg/dL. All these patients had diagnostic video-assisted thoracoscopy which was associated to talc poudrage in 50 cases. Chemotherapy by Cisplatin-Pemetrexed was administered in all the cases, which was used for induction purposes in 13 cases and as definitive treatment in the remaining patients. Extrapleural pneumonectomy could be carried out in all the 13 patients in whom it was initially planned.

Expression of NTS and NTSR1 in Malignant Pleural Mesothelioma: Immunohistochemistry.

Figure 1:
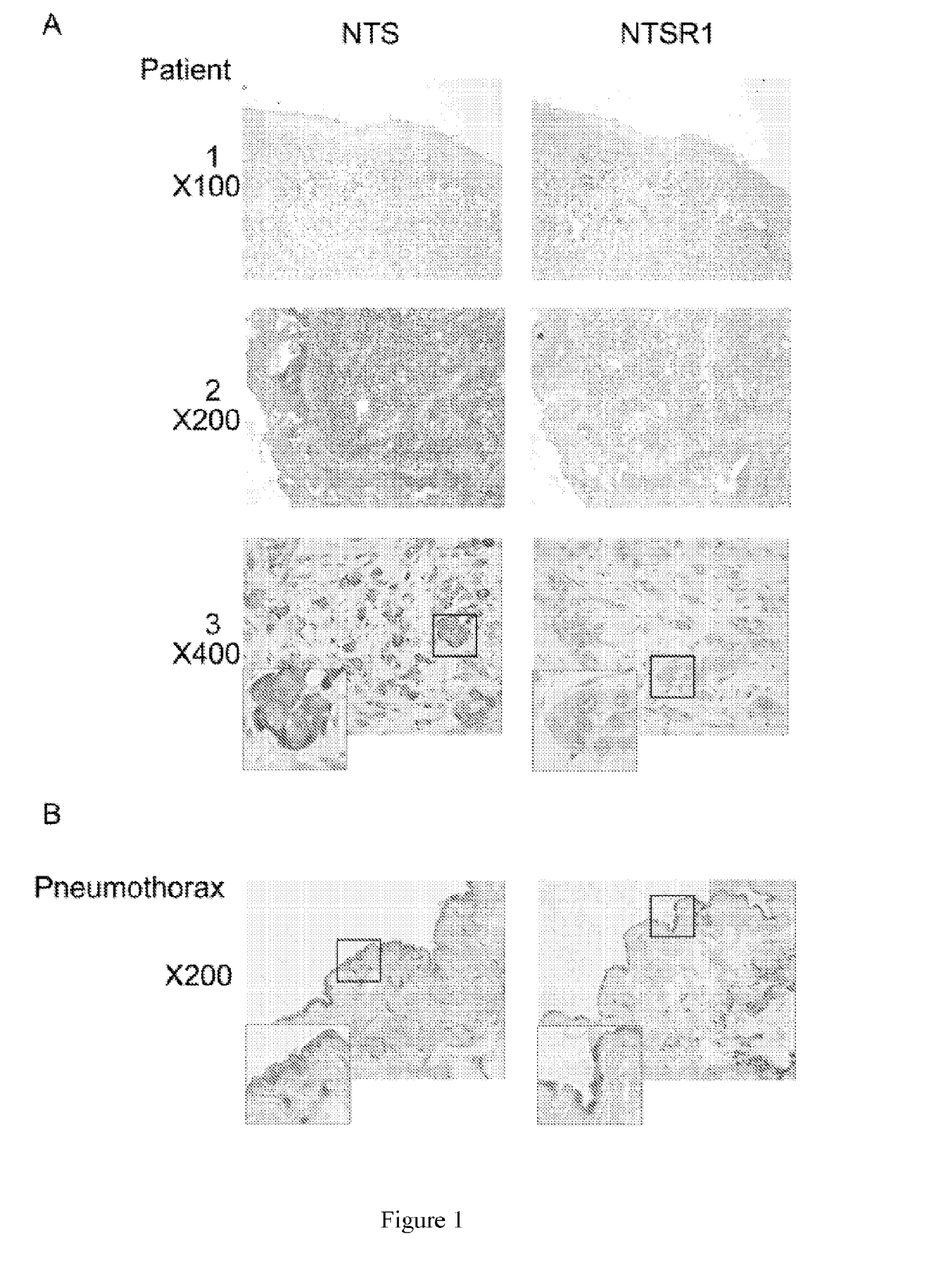
FIG. 1: NTS (left) and NTSR1 (right) expression in patients with malignant pleural mesothelioma (A), or with idiopathic spontaneous pneumothorax (B). (A) Examples of immunohistochemistry of three different patients are shown. For patient 1 and 2 consecutive slide were used. Original magnifications are noted on the Figure. Inset show computerized enlargement of a region of interest, the black squares localize the image with a black contour. Positivity was scored by an anatomopathologist
Figure 2:
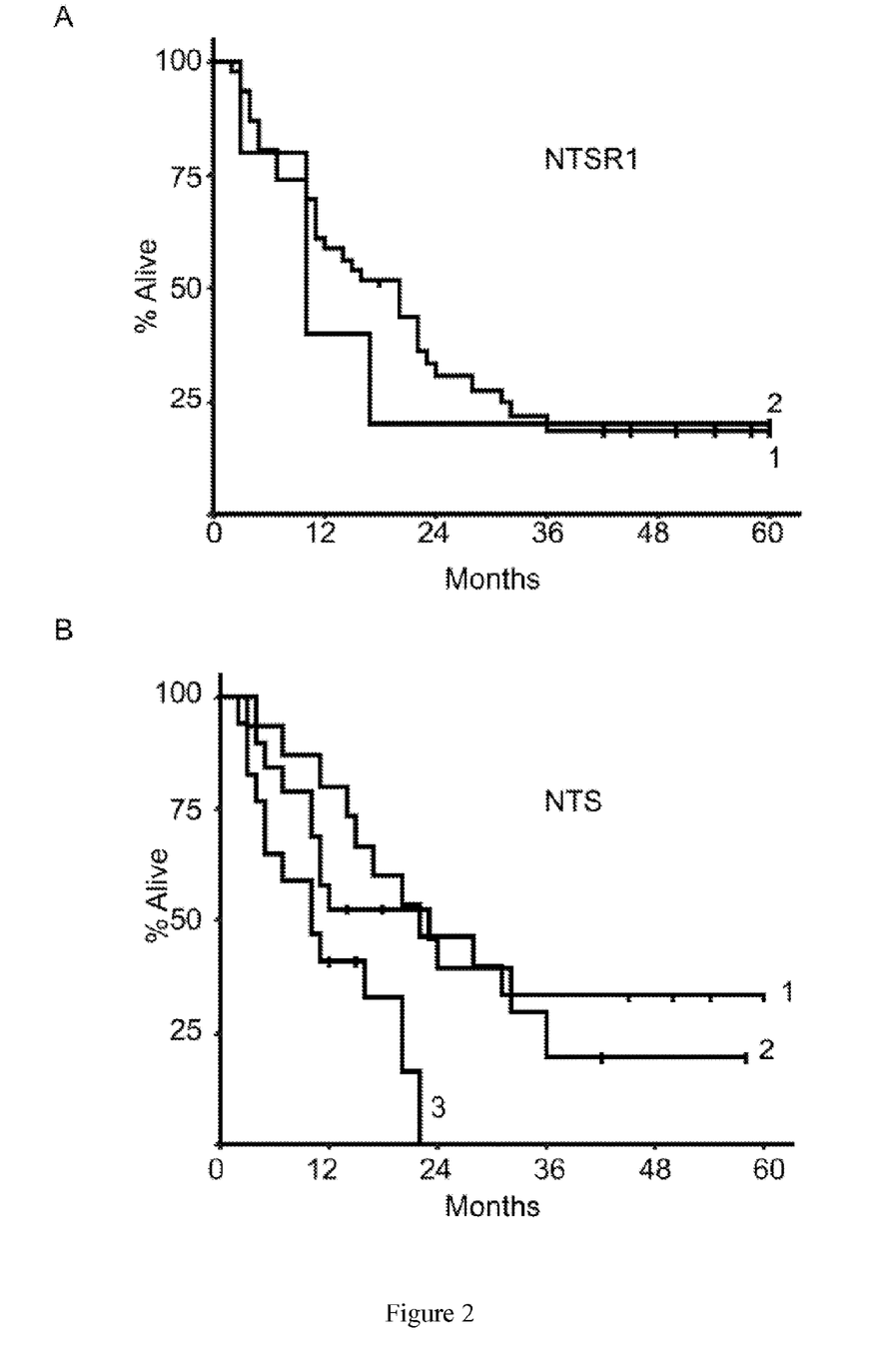
FIG. 2: NTSR1 and NTS expression in pleural mesothelioma and global survival at five-year duration.

NTS labeling was often very intense and was always detected throughout the entire cytosol. For the most part, all cancer cells were labeled, whereas the tumor stroma was negative. A typical image of the observed NTS immunostaining is shown in FIG. 1A right. NTSR1 staining of cancer cells from patients with MPM was granular, mainly restricted to the cytoplasm, and rarely detected at the cell surface, as shown FIG. 1A left. Expression of NTS was found in 37/52 cases (71.1%) and scored 0 (no expression), 1 and 2 in 15, 20, and 17 cases, respectively. Expression of NTSR1 was found in 47/52 cases (90.4%) and scored as 0; 1 and 2 in 5, 35, and 12 cases, respectively. In pleura of patients treated for idiopathic spontaneous pneumothorax, expression of NTS and NTSR1 was observed in 8/26 (31%) and 20/26 (77%) cases, respectively, whereas no expression of either NTS or NTSR1 was observed in the pulmonary parenchyma of apical resection specimens. Of note, NTSR1 staining in pleural of patients with pneumothorax was different as compared to MPM, as it was in almost all the cases restricted to the cell membrane (FIG. 1B inset magnification). Expression of NTSR1, as assessed by immunohistochemistry, had no impact on survival in patients with MPM (FIG. 2A). On the other hand, the expression of NTS was associated with a significantly (p=0.015) worse prognosis: median survivals were 29.8 months, 18.4 months, and 11 months in patients having NTS expression scored as 0, 1, and 2, respectively. Five-year survival was 33.3% (95% C.I. 15-2-58.3 months) in patients with no NTS expression as compared to 0% in case of positive staining (FIG. 2B).

With respect to other clinical parameters possibly influencing survival, no difference in terms of survival was observed using univariate analysis according to sex and age. High levels of CRP (>50 mg/L) were associated with a strong trend toward poor prognosis (p=0.061). On the other hand patients treated by extra-pleural pneumonectomy showed a trend (p=0.075) toward better prognosis as compared to patients not receiving this surgical treatment (5-year survival rates of 42.3% [95% C.I. 19.8%-68.6%] vs 11.0% [95% C.I. 4.0-27.1%], respectively). Using multivariate analysis only expression of NTS1 (p=0.007) and a non-surgical treatment (p=0.04) negatively affected the outcome.

Expression of the NTS and NTSR1 in MSTO-211H Cell Line

Figure 3:
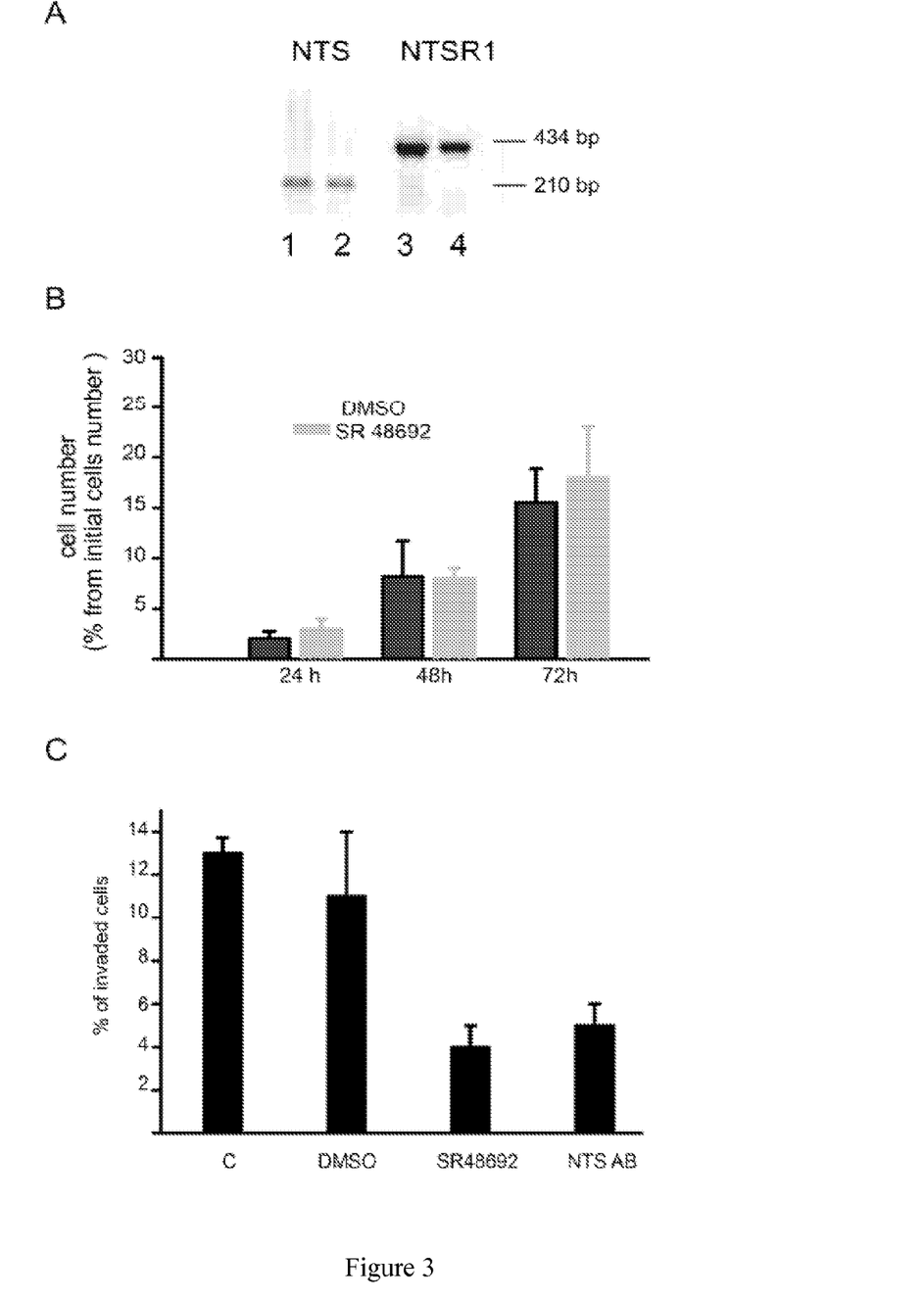
FIG. 3: Effect of NTSR1 antagonist on MSTO-211H cell growth and invasion.

Expression of both NTS and NTSR1 in human malignant mesothelioma MSTO-211 has been investigated in the present study. Two specific PCR amplicons with a size of 210 bp and 434 bp, corresponding respectively to NTS and NTSR1, were detected (FIG. 3A lane 2 and 4). Correspondence was verified by comparison to the positive control cell line, LNM 35, known to express the peptide and the receptor, (FIG. 3A lane 1 and 3).

Cellular Effects of NTS/NTSR1 Complex Inhibition.

Figure 4:
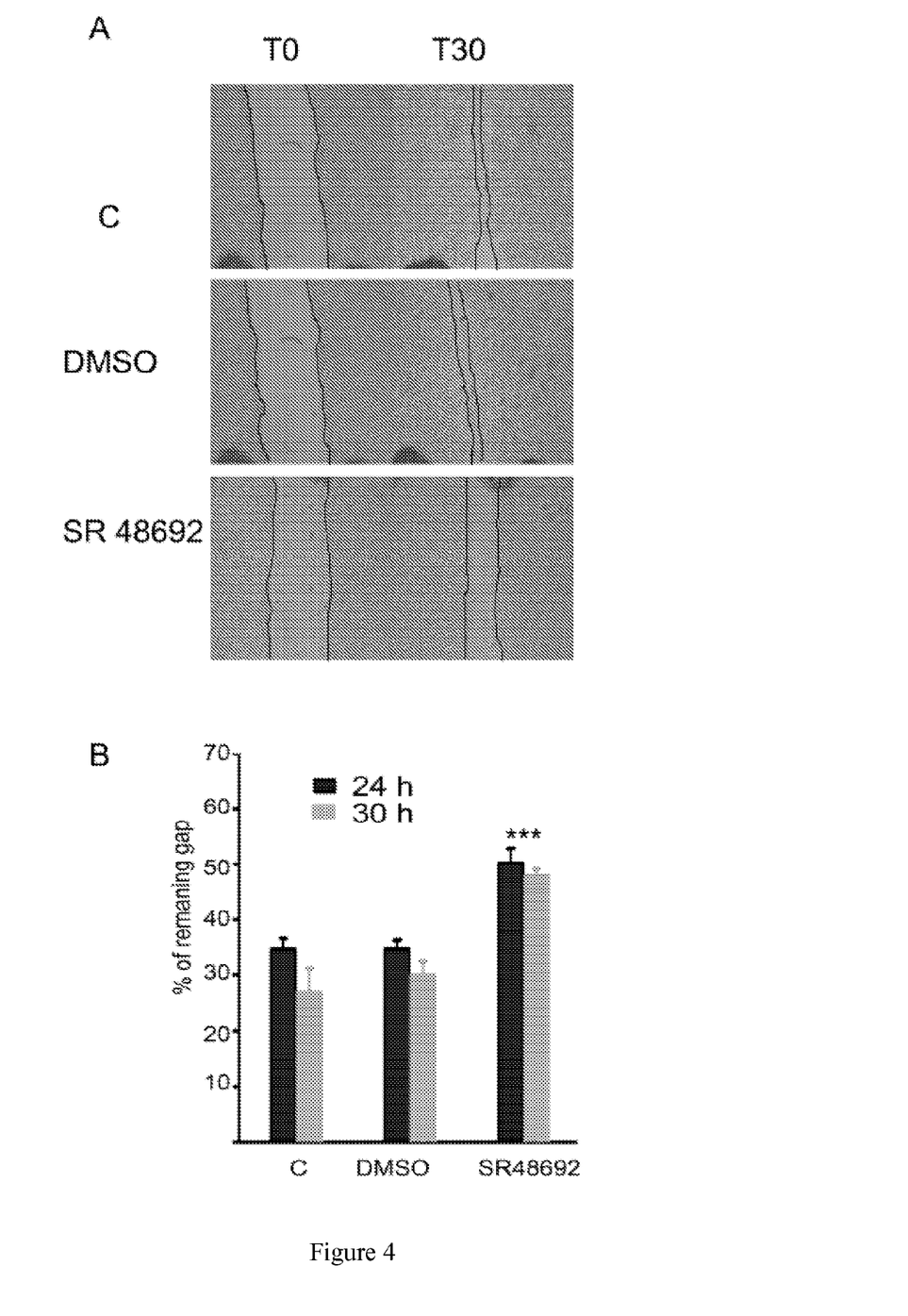
FIG. 4: Effect of NTSR1 blockade on cellular migration. Wound repair process was studied on MSTO-211H in the presence or absence of NTSR1 antagonist, SR48692.

As shown in FIG. 3 B, inhibition of neurotensinergic system, by the presence in the culture media, of a specific NTSR1 antagonist, SR 48692 had no effect on cell growth. However, MSTO-211H invasivness ability is decreased when SR48692 or blocking NTS antibody is present in the culture media, only 4% and 5% of cells invaded the type I collagen, respectively, as compared to 13% (untreated cells) and 11% (supplemented with DMSO) in the control groups (FIG. 3C). The wound healing assay showed a residual gap at 24 and 30 hours was larger (48% of original gap) when cells are treated with SR48692 as compared to control treatments, 27% and 30% of original gap in untreated cells or in the presence of DMSO, respectively (FIGS. 4 A and B). Wound closure process after scarification of the cell layer, and the cellular invasion activity are therefore affected by selective pharmacological blockade of NTSR1.

Discussion

In the present study we report evidence that a strong NTS expression is associated with poor long term outcome in patients with epithelioid malignant pleural mesothelioma. This was confirmed by multivariate analysis which showed that in experimental population, only the expression of NTS and the absence of surgery with curative intent (extra-pleural pneumonectomy) were independent predictors of poor 5-year survival. NTS staining was found in 61% of the mesothelioma samples, but less frequently (30%. of cases) and with a slighter intensity in normal pleura specimens. The percentage of specimen expressing NTSR1 was high in both normal pleura and mesothelioma, however the expression pattern was different, as a thin, peripheral (membranous) staining was generally observed in normal tissue, whereas a strong intracellular staining was seen in mesothelioma samples, suggesting an active endocytosis process of the receptor in the latter. This suggests that the NTS/NTSR1 system is relatively quiescent in normal tissue, as opposed to a condition of sustained activation in mesothelioma samples, which possibly lead to oncogenic NTS effects occurring and participate to tumorigenesis and progression of mesothelioma.

In the clinical evolution of mesothelioma local growth and cellular migration inside the pleural cavity and invasion of the neighboring structure represent characteristic features, whereas distant metastasis often occur relatively late in the evolution of the disease. We addressed the NTS potential role in these processes, using cellular model expressing endogenously NTS and NTSR1, the MSTO-211H cells. NTS/NTSR1 blockade by a specific NTSR1 antagonist or NTS blocking anti sera strongly reduced invasion and mobility cellular activity. Recently, it was shown that NTSR1 activation elicits IKB-alpha degradation and NF-KB activation with subsequent expression and released of IL-8. IL-8 has been shown to be an important mediator in the development of pleural effusion in mesothelioma; and represents an autocrine growth factor for malignant pleural mesothelioma. Thus NTS induced chemokine expression and cell migration provide a strong hypothetic role for NTS in the pathogenesis of clinical manifestations of mesothelioma.

The availability of useful prognostic factors in mesothelioma is made difficult due to the extreme heterogeneousness of patient populations, in terms of histological typing, disease staging, and type of treatments. For these reasons, we focused our approach on studying patients whose disease was accessible to a treatment with possibly curative intent. In our series, overall 5-year survival was 19%, and the relative figure were 42.3% and 11% in patients receiving, or not, extrapleural pneumonectomy as a part of their management. All these figures were in agreement with currently available data on patients receiving a similar management. In this selected patient population, we found that only high pre-operative CRP levels (an already known prognostic marker), a non-surgical treatment, and high expression of NTS negatively affected outcome (the significance was reached for NTS, whereas p values were close to significance for CRP and exptrapleural pneumonectomy treatment), with only the last two parameters being significant at multivariate analysis. Importantly among patients with high expression of NTS (scored=2) no survivor was observed beyond 22 months after histological diagnosis. Thus high NTS expression could help in identification of patients requiring stricter follow-up and/or a even more aggressive treatment.

Our clinical and experimental data indicates that the NTS/NTSR1 complex is not only a potential marker of negative prognosis, but also a mediator of disease progression.

REFERENCES

Throughout this application, various references describe the state of the art to which this invention pertains. The disclosures of these references are hereby incorporated by reference into the present disclosure.

The invention claimed is:

1. A method for the treatment of malignant pleural mesothelioma, wherein an inhibitor of the neurotensin activation of neurotensin receptor 1 (NTSR1) is administered to a subject in need thereof.

2. The method of claim 1, wherein said inhibitor of the neurotensin activation of NTSR1 is an agent down-regulating the expression of neurotensin or of NTSR1.

3. The method of claim 1, wherein said inhibitor of the neurotensin activation of NTSR1 is selected from the group consisting of an antibody against neurotensin, a fragment thereof which binds to neurotensin, an antibody against the neurotensin receptor 1 and a fragment thereof which binds to the neurotensin receptor 1.

4. The method of claim 1, wherein said inhibitor of the neurotensin activation of NTSR1 is an antagonist of NTSR1.

5. The method of claim 1, wherein said inhibitor of the neurotensin activation of NTSR1 is a protease that can degrade neurotensin.

* * * * *

UNITED STATES PATENT AND TRADEMARK OFFICE
CERTIFICATE OF CORRECTION

PATENT NO.         : 8,771,691 B2  
APPLICATION NO.    : 13/139907  
DATED              : July 8, 2014  
INVENTOR(S)        : Patricia Forgez et al.

Page 1 of 1

It is certified that error appears in the above-identified patent and that said Letters Patent is hereby corrected as shown below:

On the Title Page, in Item (73), under "ASSIGNEE," please correct the Assignee names to read:

--INSERM (INSTITUT NATIONAL DE LA SANTE ET DE LA RECHERCHE MEDICALE)--
--ASSISTANCE PUBLIQUE HOPITAUX DE PARIS--

Signed and Sealed this
Fourth Day of November, 2014

Michelle K. Lee
*Deputy Director of the United States Patent and Trademark Office*

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial
<220> FEATURE:
<223> OTHER INFORMATION: siRNA

<400> SEQUENCE: 1
aagaagttca tcagcgccat c                                             21

<210> SEQ ID NO 2
<211> LENGTH: 19
<212> TYPE: DNA
<213> ORGANISM: Artificial
<220> FEATURE:
<223> OTHER INFORMATION: siRNA

<400> SEQUENCE: 2
gcaatgttga caatatacc                                                19

<210> SEQ ID NO 3
<211> LENGTH: 15
<212> TYPE: DNA
<213> ORGANISM: Artificial
<220> FEATURE:
<223> OTHER INFORMATION: primer

<400> SEQUENCE: 3
gctgacgtag aagag                                                    15

<210> SEQ ID NO 4
<211> LENGTH: 20
```

```
<212> TYPE: DNA
<213> ORGANISM: Artificial
<220> FEATURE:
<223> OTHER INFORMATION: primer

<400> SEQUENCE: 4
cgtggagctg tacaacttca                                       20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cagccagcag accacaaagg                                       20

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
aagcacatgt tccctctt                                         18

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
catacagctg ccgtttcaga                                       20
```